United States Patent [19]

Shen et al.

[11] 4,202,903

[45] May 13, 1980

[54] ACYL CYANOGUANIDINES FOR TREATING RHEUMATOID ARTHRITIS

[75] Inventors: Tsung-Ying Shen, Westfield; Howard Jones, Holmdel, both of N.J.

[73] Assignee: Merck & Co., Inc., Rahway, N.J.

[21] Appl. No.: 618,108

[22] Filed: Sep. 30, 1975

[51] Int. Cl.$^2$ ............................................. A61K 31/155
[52] U.S. Cl. .................................................... 424/326
[58] Field of Search ......................................... 424/326

[56] References Cited

U.S. PATENT DOCUMENTS

| | | | |
|---|---|---|---|
| 2,315,765 | 4/1943 | Bindler | 260/551 C |
| 2,407,161 | 9/1946 | Kaiser et al. | 260/551 C |

*Primary Examiner*—Frederick E. Waddell
*Attorney, Agent, or Firm*—Raymond M. Speer; Harry E. Westlake

[57] ABSTRACT

Certain novel acyl cyanoguanidines, their preparation, pharmaceutical compositions and novel methods of treating inflammation and autoimmune diseases such as rheumatoid arthritis are disclosed.

1 Claim, No Drawings

ACYL CYANOGUANIDINES FOR TREATING RHEUMATOID ARTHRITIS

BACKGROUND OF THE INVENTION

In spite of the extensive antiinflammatory research in the past two decades there is still an obvious need for an effective and well-tolerated agent for the treatment of rheumatoid arthritis. Conventional antiinflammatory-analgesic-antipyretic agents, such as aspirin, and many experimental new drugs under clinical evaluation, are mostly effective in providing symptomatic relief of the acute syndrome only. As a consequence, the antirheumatic actions of two other remedies, gold and particularly D-penicillamine, have received renewed interest in the past few years. The clinical efficiancy of both drugs has been confirmed by well-controlled multi-center clinical studies. Impressed by these findings, a growing population of rheumatologists have expressed the opinion that compounds possessing properties similar to D-penicillamine should be a valuable contribution to medicine in this important field. Thus it is an important discovery that acyl cyanoguanidines possess immunological properties similar to that of D-penicillamine, being of value in the treatment of rheumatoid arthritis and related inflammatory disorders, as well as antiinflammatory properties.

DETAILED DESCRIPTION OF THE INVENTION

This invention relates to a novel class of acyl cyanoguanidines, useful for treating inflammation and autoimmune diseases, such as rheumatoid arthritis. The novel acyl cyanoguanidines of this invention have the following structural formula:

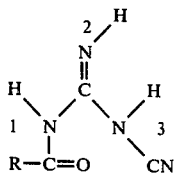

I wherein R is $C_{1-7}$alkyl, substituted $C_{1-7}$alkyl, $C_{1-5}$alkoxy, phenyl, substituted phenyl, heteroaryl, substituted heteroaryl or adamantyl, wherein substituted $C_{1-7}$alkyl is $C_{1-7}$alkyl substituted with one or more $C_{1-3}$alkyl or halo groups, substituted phenyl is phenyl substituted with one or more hydroxy, mercapto, halo, cyano, phenyl, carboxymethylthio, nitro, amino, N-$C_{1-5}$alkylamino or N,N-di$C_{1-5}$alkylamino groups, heteroaryl is thienyl, furyl, pyrrolyl, pyridyl and substituted heteroaryl is heteroaryl as defined above substituted with one or more hydroxy, $C_{1-5}$alkoxy, mercapto, $C_{1-5}$alkylthio, $C_{1-5}$alkylsulfinyl, $C_{1-5}$alkylsulfonyl, halo, cyano, phenyl, carboxymethylthio, nitro, amino, N-$C_{1-5}$alkylamino or N,N-di$C_{1-5}$alkylamino. The substituted phenyl and substituted heteroaryl groups are preferably monosubstituted and include the various position isomers of the various substitutent groups on the aromatic rings, such as ortho, meta and para for phenyl, 2,3,4 or 5 for 5-membered heterocyclic rings (thienyl, furyl or pyrrolyl) and 2,3,4, 5 or 6 for 6-membered heterocyclic rings (pyridyl). In a preferred embodiment, R is methyl, ethoxy, 3-pentyl, phenyl, halophenyl, thienyl, halothienyl, $C_{1-5}$alkoxythienyl, $C_{1-5}$alkylthiothienyl or adamantyl. In a more preferred embodiment, R is fluorophenyl, thienyl, or adamantyl.

The following novel compounds are representative of this invention:

1-propionyl-3-cyanoguanidine,
1-(2'-ethylhexanoyl)-3-cyanoguanidine,
1-trifluoroacetyl-3-cyanoguanidine,
1-α-chloroacetyl-3-cyanoguanidine,
1-α-fluoroacetyl-3-cyanoguanidine,
1-propoxycarbonyl-3-cyanoguanidine,
1-butoxycarbonyl-3-cyanoguanidine,
1-t-butoxycarbonyl-3-cyanoguanidine,
1-phenyl-3-cyanoguanidine,
1-(3'-fluorobenzoyl)-3-cyanoguanidine,
1-(2'-chlorobenzoyl)-3-cyanoguanidine,
1-(4'-chlorobenzoyl)-3-cyanoguanidine,
1-(2'-bromobenzoyl)-3-cyanoguanidine,
1-(3'-nitrobenzoyl)-3-cyanoguaindine,
1-(3'-aminobenzoyl)-3-cyanoguanidine,
1-(3'-N-methylaminobenzoyl)-3-cyanoguanidine,
1-(3'-N,N-dimethylaminobenzoyl)-3-cyanoguanidine,
1-(2'-hydroxybenzoyl)-3-cyanoguanidine,
1-(2'-mercaptobenzoyl)-3-cyanoguanidine,
1-(2'-cyanobenzoyl)-3-cyanoguanidine,
1-(2'-phenylbenzoyl)-3-cyanoguanidine,
1-(2'-carboxymethylthiobenzoyl)-3-cyanoguanidine,
1-(2'-furoyl)-3-cyanoguanidine,
1-(2'-pyrrolylcarbonyl)-3-cyanoguanidine
1-(2'-pyridylcarbonyl)-3-cyanoguanidine,
1-[2'-(3'-fluorothienyl)]-3-cyanoguanidine,
1-[2'-(3'-chlorothienyl)]-3-cyanoguanidine,
1-[2'-(3'-bromothienyl)]-3-cyanoguanidine,
1-[2'-(3'-methoxythienyl)]-3-cyanoguanidine,
1-[2'-(3'-ethoxythienyl)]-3-cyanoguanidine,
1-[2'-(3'-methylthioyl)]-3-cyanoguanidine,
1-[2'-(3'-ethylthiothienyl)]-3-cyanoguanidine,
1-[2'-(3'-methylsulfinylthienyl)]-3-cyanoguanidine,
1-[2'-(3'-methylsulfonylthienyl)]-3-cyanoguanidine,
1-[2'-(3'-hydroxythienyl)]-3-cyanoguanidine,
1-[2'-(3'-methylsulfinylthienyl)]-3-cyanoguanidine,
1-[2'-(3'-methylsulfonylthienyl)]-3-cyanoguanidine,
1-[2'-(3'-cyanosulfonylthienyl)]-3-cyanoguanidine,
1-[2'-(3'-nitrothienyl)]-3-cyanoguanidine,
1-[2'-(3'-aminothienyl)]-3-cyanoguanidine,
1-[2'-(3'-N-methylaminothienyl)]-3-cyanoguanidine,
1-[2'-(3'-N,N-dimethylaminothienyl)]-3-cyanoguanidine,
1-[3'-(4'-methoxyfuroyl)]-3-cyanoguanidine,
1-[3'-(4'-fluorofuroyl)]-3-cyanoguanidine,
1-[3'-(4'-chlorofuroyl)]-3-cyanoguanidine,
1-[3'-(4'-methylthiofuroyl)]-3-cyanoguanidine,
1-[3'-(4'-methoxypyrrolylcarbonyl)]-3-cyanoguanidine,
1-[3'-(4'-fluoropyrrolylcarbonyl)]-3-cyanoguanidine,
1-[3'-(4'-chloropyrrolylcarbonyl)]-3-cyanoguanidine,
1-[3'-(4'-methoxynicotinyl)]-3-cyanoguanidine,
1-[3'-(4'-fluoronicotinyl)]-3-cyanoguanidine,
1-[3'-(4'-chloronicotinyl)]-3-cyanoguanidine or
1-[3'-(4'-methylthionicotinoyl)]-3-cyanoguanidine.

Another aspect of this invention relates to the novel pharmaceutical compositions for treating inflammation and autoimmune diseases, such as rheumatoid arthritis, comprising a non-toxic pharmaceutically acceptable carrier and a compound of the formula I, supra, wherein R is as defined above.

The non-toxic pharmaceutical carrier may be, for example, either a solid or a liquid. Exemplary of solid carriers are lactose, corn starch, gelatin, talc, sterotix, stearic acid, magnesium stearate, terra alba, sucrose, agar, pectin and acacia. Exemplary of liquid carriers are peanut oil, olive oil, seasame oil and water. Similarly the carrier or diluent may include a time delay material such as glyceryl monostearate or glyceryl distearate, alone, or with a wax.

The treatment of inflammation and autoimmune diseases, such as rheumatoid arthritis, in accordance with the method of the present invention is accomplished by orally, rectally, parenterally or topically administering to patients the compounds of formula I, supra, or mixtures thereof in a non-toxic pharmaceutically acceptable carrier.

Several pharmaceutical forms of the therapeutically useful compositions may be used. For example, if a solid carrier is used, the compositions may take the form of tablets, capsules, powders, troches or lozenges, prepared by standard pharmaceutical techniques. If a liquid carrier is used, the preparation may be in the form of a soft gelatin capsule, a syrup, a liquid solution, a liquid emulsion or a liquid suspension. Suppositories may be prepared in the conventional manner by mixing the compounds of this invention with a suitable non-irritating excipient which is solid at room temperature. Exemplary of excipients are cocoa butter and polyethylene glycol. Gels, lotions and aerosol sprays for topical application may be prepared in conventional manners.

The active compounds are administered in a therapeutically effective amount sufficient to treat inflammation and autoimmune diseases such as rheumatoid arthritis. The treatment of rheumatoid arthritis is one condition where the treatment of inflammation and the autoimmune disorder will improve the condition, and accordingly the amount of active compound necessary to treat inflammation and the autoimmune disorder is the amount required to treat the rheumatoid arthritis. Advantageously, the active compounds will be administered, alone or in a pharmaceutical composition in an amount of from about 1.0 mg to 100 mg per kg body weight per day (50 mg to 5.0 g per patient per day of the active compound) preferably from about 1.5 mg to 15 mg per kilogram body weight per day. The daily dosage may be given in either single or multiple dosages.

The method of treatment of this invention comprises administering to a patient (animal or human) the compound as previously described admixed with a nontoxic pharmaceutical carrier such as exemplified above. It should be understood that although preferred dosage ranges are given, the dose level for any particular patient depends upon the activity of the specific compound employed. Also many other factors that modify the actions of drugs will be taken into account by those skilled in the art in the therapeutic use of medicinal agents, particularly those described above; for example, body weight, sex, diet, time of administration, route of administration, rate of excretion, drug combination, reaction sensitivities and severity of the particular disease.

Another aspect of this invention is the process for preparing the novel compounds of formula I, supra, wherein R is as defined above, by reacting a compound of the formula:

II wherein X is halo, such as chloro or bromo, with a compound of the formula:

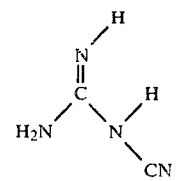

III

The compound of formula III, supra, also known as dicyanodiamide or cyanoguanidine, exists in several tautomeric forms. Reactants II and III are present in approximately equal molar amounts.

The reaction may be carried out in a suitable solvent. The solvent may be a ketone, such as acetone or methyl ethyl ketone, an ether, such as diethyl ether, a cyclic ether, such as tetrahydrofuran (THF) or dioxan, an amide, such as dimethylformamide (DMF), dimethylacetamide (DMA) or hexamethylphosphoramide (HMPA), a hydrocarbon such as benzene, toluene or xylene, a pyridine or a tri($C_{1-3}$-alkyl)amine.

The reaction may also be carried out in the presence of a base in an equal molar or greater amount to remove the hydrogen halide formed by the reaction. If the base is a liquid, such as a pyridine or a tri($C_{1-3}$alkyl)amine, it may also serve as the solvent. Other bases which may be used are the alkali metal hydroxides, amides, carbonates or bicarbonates and the alkaline earth hydroxides, oxides, carbonates and bicarbonates. Examples of suitable bases are sodium hydroxide, potassium hydroxide, calcium carbonate, pyridine and triethylamine.

The reaction temperature is not critical and generally the reacton is carried out at a temperature of from about $+20°$ C. to $-30°$ C., preferably at ambient temperatures. The time of reaction is not critical and generally the reaction is carried out until it is essentially complete. The pressure is not critical and generally the reaction is carried out at atmospheric pressure in an open system. The product of the reaction, a compound of formula I, may be recovered in the conventional manner, such as by extraction or crystallation.

The starting materials employed in the foregoing processes have been described in the literature and many are commercially available, except as described below. Various substituents may be introduced into the aromatic rings by well known methods, such as nitration for the nitro group; reduction of the nitro group to an amino group with either hydrogen and a catalyst, such as Raney nickel, finely divided platinum or palladium or with finely divided tin and hydrochloric acid; reductive alkylation of the nitro group to produce a $C_{1-5}$alkylamino or di$C_{1-5}$alkylamino group by conducting the catalytic hydrogenation in the presence of a $C_{1-5}$alkylaldehyde; $C_{1-5}$alkylation of the amino group with a $C_{1-5}$alkylaldehyde to produce either a $C_{1-5}$alkylamino or a di$C_{1-5}$alkylation group; or diazotization of the amino group followed by reaction with (a) water, sulfuric acid and heat (95° C.) to produce the hydroxyl group; (b) potassium iodide and heat (95° C.) to produce the iodo group; (c) cuprous chloride to produce the chloro group; (d) cuprous cyanide and potassium cyanide to produce the cyano group; (e) hydrobromic acid and powdered metallic copper to produce the bromo group; (f) powdered copper or zinc and benzene to produce the phenyl group; (g) potassium mercaptide to produce the mercapto group; (h) thioglycolic acid to produce the carboxymethylthio group; or (i) fluoboric acid to produce the fluoro group. The carboxylic acids may be converted to the corresponding acid halides by reaction with a halogenating agent such as phosphorous trihalide, phosphorous pentahalide, carbonyl halide and thionyl halide. Examples of suitable halogenating agents are phosphorous trichloride, and thionyl chloride.

The following examples are given to illustrate the invention and are not intended to limit it in any manner. All parts are given in parts by weight unless otherwise expressed.

EXAMPLE 1

1-(4'-Fluorobenzoyl)-3-cyanoguanidine

A. 4-Fluorobenzoyl chloride

4-Fluorobenzoic acid, 14.0 g (0.1 mole) is refluxed for 30 minutes in 50 ml of thionyl chloride ($SOCl_2$) and 1 drop of dimethylformamide (DMF). The thionyl chloride is removed under vacuum and azeotroped with 50 ml of benzene to give 4-fluorobenzoyl chloride as an oil.

Similarly, when an equivalent amount of acetic acid, 3-pentanecarboxylic acid, 2-thiophenecarboxylic acid, 1-adamantanecarboxylic acid, benzoic acid or 2-fluorobenzoic acid is substituted for the 4-fluorobenzoic acid in the above example, there is obtained acetyl chloride, 2-ethylbutyryl chloride, 2-thenoyl chloride, 1-adamantylcarbonyl chloride, benzoyl chloride or 2-fluorobenzoyl chloride.

B. 1-(4'-Fluorobenzoyl)-3-cyanoguanidine

Potassium hydroxide, 13.02 g (0.2 mole) is dissolved in 40 ml of water and 10.51 g (0.125 mole) of dicyanodiamide is added, followed by the addition of 50 ml of acetone. The mixture is cooled to 0° C. and the 4-fluorobenzoyl chloride from Step 1A, above, is added dropwise. The mixture is stirred at 0° C. for 1 hour and placed in the refrigerator overnight. The mixture is poured into 500 ml of water and the water is then acidified with an excess of acetic acid. The product forms a precipitate which is filtered, washed with water followed by ether and air dried to give 10.1 g of 1-(4'-fluorobenzoyl)-3-cyanoguanidine, m.p. 322° C. dec.

Similarly, when an equivalent amount of ethyl chloroformate, acetyl chloride, 2-ethylbutyryl chloride, 2-thenoyl chloride, 1-adamantylcarbonyl chloride, benzoyl chloride or 2-fluorobenzoyl chloride is substituted for the 4-fluorobenzoyl chloride in the above example, there is obtained 1-ethoxycarbonyl-3-cyanoguanidine, m.p. greater than 330° C.; 1-acetyl-3-cyanoguanidine, m.p. greater than 250° C.; 1-(2'-ethylbutyryl)-3-cyanoguanidine, m.p. 140°–142° C.; 1-(2-thenoyl)-3-cyanoguanidine, m.p. 204°–205° C.; 1-adamantylcarbonyl-3-cyanoguanidine, m.p. 193°–194° C.; 1-benzoyl-3-cyanoguanidine; or 1-(2'-fluorobenzoyl)-3-cyanoguanidine, m.p. 181°–182° C.

EXAMPLE 2

A mixture of 250 parts of 1-(4'-fluorobenzoyl)-3-cyanoguanidine and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

Similarly, an equivalent amount of 1-ethoxycarbonyl-3-cyanoguanidine, 1-acetyl-3-cyanoguanidine, 1-(2'-ethylbutyryl)-3-cyanoguanidine, 1-(2'-thenoyl)-3-cyanoguanidine, 1-adamantylcarbonyl-3-cyanoguanidine, 1-benzoyl-3-cyanoguanidine or 1-(2'-fluorobenzoyl)-3-cyanoguanidine may be substituted for the 1-(4'-fluorobenzoyl)-3-cyanoguanidine in the above pharmaceutical composition.

EXAMPLE 3

A mixture of 50 parts of 1-(4'-fluorobenzoyl)-3-cyanoguanidine, 3 parts of the calcium salt of lignin sulphonic acid, and 237 parts of water is ball-milled until the size of substantially all of the particles of the acid is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

Similarly, an equivalent amount of 1-ethoxycarbonyl-3-cyanoguanidine, 1-acetyl-3-cyanoguanidine, 1-(2'-ethylbutyryl)-3-cyanoguanidine, 1-(2'-thenoyl)-3-cyanoguanidine, 1-adamantylcarbonyl-3-cyanoguanidine, 1-benzoyl-3-cyanoguanidine or 1-(2'-fluorobenzoyl)-3-cyanoguanidine may be substituted for the 1-(4'-fluorobenzoyl)-3-cyanoguanidine in the above pharmaceutical composition.

EXAMPLE 4

A mixture of 250 parts of 1-(4'-fluorobenzoyl)-3-cyanoguanidine, 200 parts of maize starch and 30 parts of alginic acid is mixed with a sufficient quantity of 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

Similarly, an equivalent amount of 1-ethoxycarbonyl-3-cyanoguanidine, 1-acetyl-3-cyanoguanidine, 1-(2'-ethylbutyryl)-3-cyanoguanidine, 1-(2'-thenoyl)-3-cyanoguanidine, 1-adamantylcarbonyl-3-cyanoguanidine, 1-benzoyl-3-cyanoguanidine or 1-(2'-fluorobenzoyl)-3-cyanoguanidine may be substituted for the 1-(4'-fluorobenzoyl)-3-cyanoguanidine in the above pharmaceutical composition.

EXAMPLE 5

A mixture of 500 parts of 1-(4'-fluorobenzoyl)-3-cyanoguanidine, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into table form suitable for oral administration.

Similarly, an equivalent amount of 1-ethoxycarbonyl-3-cyanoguanidine, 1-acetyl-3-cyanoguanidine, 1-(2'-ethylbutyryl)-3-cyanoguanidine, 1-(2'-thenoyl)-3-cyanoguanidine, 1-adamantylcarbonyl-3-cyanoguanidine, 1-benzoyl-3-cyanoguanidine or 1-(2'-fluorobenzoyl)-3-cyanoguanidine may be substituted for the 1-(4'-fluorobenzoyl)-3-cyanoguanidine in the above pharmaceutical composition.

EXAMPLE 6

1. Tablets—10,000 scored tablets for oral use, each containing 500 mg. of active ingredient are prepared from the following ingredients:

|  | G. |
| --- | --- |
| 1-(4'-fluorobenzoyl)-3-cyanoguanidine) | 5000 |
| Starch, U.S.P. | 350 |
| Talc, U.S.P. | 250 |
| Calcium stearate | 35 |

The powdered 1-(4'-fluorobenzoyl)-3-cyanoguanidine is granulated with a 4% w./v. aqueous solution of methylcellulose U.S.P. (1,500 cps.). To the dried granules is added a mixture of the remainder of the ingredients and the final mixture compressed into tablets of proper weight.

2. Capsules—10,000 two-piece hard gelatin capsules for oral use, each containing 250 mg. of 1-(4'-fluorobenzoyl)-3-cyanoguanidine are prepared from the following ingredients:

|  | G. |
| --- | --- |
| 1-(4'-fluorobenzoyl)-3-cyanoguanidine | 2500 |
| Lactose, U.S.P. | 1000 |
| Starch, U.S.P. | 300 |
| Talc, U.S.P. | 65 |
| Calcium stearate | 25 |

The powdered 1-(4'-fluorobenzoyl)-3-cyanoguanidine is mixed with the starch-lactose mixture followed by the talc and calcium stearate. The final mixture is then encapsulated in the usual manner. Capsules containing 10, 25, 50, and 100 mg. of 1-(4'-fluorobenzoyl)-3-cyanoguanidine are also prepared by substituting 100, 250, 500, and 1000 g. for 2,500 g. in the above formulation.

3. Soft elastic capsules—One-piece soft elastic capsules for oral use, each containing 200 mg. of 1-(4'-fluorobenzoyl)-3-cyanoguanidine are prepared in the usual manner by first dispersing the powdered active material in sufficient corn oil to render the material capsulatable.

4. Aqueous suspension—An aqueous suspension for oral use containing in each 5 ml., 1 g. of 1-(4'-fluorobenzoyl)-cyanoguanidine is prepared from the following ingredients.

| 1-(4'-fluorobenzoyl)-3-cyanoguanidine | g. | 2000 |
| --- | --- | --- |
| Methylparaben, U.S.P. | g. | 7.5 |
| Propylparaben, U.S.P. | g. | 2.5 |
| Saccharin sodium | g. | 12.5 |
| Glycerin | ml. | 3000 |
| Tragacanth powder | g. | 10 |
| Orange oil flavor | g. | 10 |
| F.D.& C. orange dye | g. | 7.5 |
| Deionized water, q.s. to 10 liters. | | |

Similarly, an equivalent amount of 1-ethoxycarbonyl-3-cyanoguanidine, 1-acetyl-3-cyanoguanidine, 1-(2'-ethylbutyryl)-3-cyanoguanidine, 1-(2'-thenoyl)-3-cyanoguanidine, 1-adamantylcarbonyl-3-cyanoguanidine, 1-benzoyl-3-cyanoguanidine or 1-(2'-fluorobenzoyl)-3-cyanoguanidine may be substituted for the 1-(4'-fluorobenzoyl)-3-cyanoguanidine in the above pharmaceutical compositions.

What is claimed is:

1. A method of treating rheumatoid arthritis which comprises administering to a patient a therapeutically effective amount of a compound of the formula:

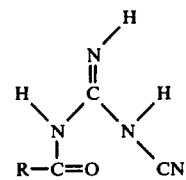

wherein R is $C_{1-7}$alkyl, substituted $C_{1-7}$alkyl, $C_{1-5}$alkoxy, phenyl or substituted phenyl, wherein substituted $C_{1-7}$alkyl is $C_{1-7}$alkyl substituted with one or more $C_{1-3}$alkyl or halo groups and substituted phenyl is phenyl substituted with one or more hydroxy, mercapto, halo, cyano, phenyl, carboxymethylthio, nitro, amino, N-$C_{1-5}$alkylamino or N,N-di($C_{1-5}$-alkyl)amino groups.

* * * * *